United States Patent [19]

Ichinose et al.

[11] Patent Number: 4,950,075
[45] Date of Patent: Aug. 21, 1990

[54] METHOD OF DETECTING AN OBJECT BY USE OF LASER LIGHT AND LASER RADAR

[75] Inventors: Yuuji Ichinose, Hitachi; Fuminobu Takahashi, Katsuta, both of Japan

[73] Assignee: Hitachi, Ltd., Tokyo, Japan

[21] Appl. No.: 346,228

[22] Filed: May 2, 1989

[30] Foreign Application Priority Data

May 2, 1988 [JP] Japan .................................. 63-109764

[51] Int. Cl.$^5$ ...................... G01B 11/26; G01N 21/00
[52] U.S. Cl. ......................................... 356/141; 356/4;
356/5; 356/152; 356/342
[58] Field of Search ...................... 356/4, 5, 141, 152,
356/342

[56] References Cited

U.S. PATENT DOCUMENTS

| | | | |
|---|---|---|---|
| 3,510,225 | 5/1970 | Collis | 356/342 |
| 3,650,627 | 3/1972 | Noxon | 356/4 |
| 3,768,908 | 10/1973 | Zaromb | 356/342 |
| 4,502,782 | 3/1985 | Werner et al. | 356/5 |

Primary Examiner—Stephen C. Buczinski
Attorney, Agent, or Firm—Antonelli, Terry, Stout & Kraus

[57] ABSTRACT

A method and an apparatus are disclosed in which paying attention to the fact that the rate of attenuation of laser lilght propagating in the atmosphere changes depending on meteorological conditions, the rate of attenuation is detected and the optimum laser beam emission or divergence angle is controlled in accordance with the detected rate of attenuation. There are also disclosed a method and an apparatus in which the optimum beam angle is controlled in accordance with a distance to a target existing in the atmosphere or the shape of the target. Further, there are disclosed a method and an apparatus in which the optimum beam angle is controlled taking either two or all of the rate of attenuation, the distance to the target and the shape of the target into consideration.

17 Claims, 9 Drawing Sheets $\theta t = \theta 1$ $\theta t = \theta 2$ $\theta t = \theta 3$

METHOD OF DETECTING AN OBJECT BY USE OF LASER LIGHT AND LASER RADAR

BACKGROUND OF THE INVENTION

The present invention relates to a method of and an apparatus (laser radar) for detecting the shape and azimuth of and the distance to an object by use of laser light, and more particularly to a method and apparatus in which a desired detection ability can be obtained irrespective of any change of meteorological conditions.

In the conventional laser radar disclosed by JP-A-50-137762, a pencil beam is transmitted during a time when a target is caught and a fan beam which is divergent in a vertical direction is transmitted when the laser beam is out of the target range while the pencil beam is transmitted again when the target is acquired again.

In the above-mentioned conventional laser radar in which two kinds of laser beams having different divergence angles are used, the beam divergence angle is changed paying attention to only the capture of the target while the attenuation of laser light in the atmosphere is not taken into consideration. Since the rate of attenuation of laser light in the atmosphere changes depending on meteorological conditions, there arises a problem that a distance to a target which can be detected by a laser beam, that is, a detectable distance may be different even when the detection of the target is made with the same beam divergence angle.

SUMMARY OF THE INVENTION

An object of the present invention is to provide a method and an apparatus in which the optimum beam angle is determined considering the rate of attenuation of laser light in the atmosphere.

Another object of the present invention is to provide a method and an apparatus in which the optimum beam angle is determined considering a distance to a target existing in the atmosphere.

Still another object of the present invention is to provide a method and an apparatus in which the optimum beam angle is determined considering the shape of a target existing in the atmosphere.

A further object of the present invention is to provide a method and an apparatus in which the optimum beam angle is determined considering the rate of attenuation of laser light in the atmosphere, a distance to a target existing in the atmosphere, and the shape of the target.

A still further object of the present invention is to provide a method and an apparatus in which the optimum laser beam emission or divergence angle is controlled taking either two or all of the above-mentioned rate of attenuation, distance to the target and shape of the target into consideration.

According to one aspect of the present invention, there is provided a laser radar comprising means for measuring a visibility range, means for determining the rate of attenuation of laser light in the atmosphere from the measured visibility range and determining a laser beam angle on the basis of the determined rate of attenuation of laser light, the minimum detectable target shape (or cross section area) and the longest detectable distance, and means for making a laser beam angle variable so that it becomes equal to the determined laser beam angle.

Preferably, the means for determining the laser beam angle further establishes a search region where a search for the target is to be made, calculates a converging limit of the laser beam, and makes the laser beam angle coincident with the search region when the determined laser beam angle is wider than the search region while making the laser beam angle coincident with the converging limit when the determined laser beam angle is smaller than the converging limit.

According to another aspect of the present invention, there is provided a laser radar comprising means for transmitting a laser beam toward a structure placed at a specified distance from the laser radar in the course of search for a target to determine the rate of attenuation of laser light in the atmosphere from waves reflected from the structure and determining a laser beam angle on the basis of the determined rate of attenuation, the minimum detectable target shape (or cross section area) and the longest detectable distance, and means for making a laser beam angle variable so that it becomes equal to the determined laser beam angle.

According to still another aspect of the present invention, there is provided a laser radar comprising means for measuring the atmospheric temperature, humidity, atmospheric pressure and rainfall, means for determining the rate of attenuation of laser light in the atmosphere from the measured atmospheric temperature, humidity, atmospheric pressure and rainfall and determining a laser beam angle on the determined rate of attenuation, the minimum detectable target shape and the longest detectable distance, and means for making a laser beam angle variable so that it becomes equal to the determined laser beam angle.

According to a further aspect of the present invention, there is provided a scanning method for a laser radar in which each time the scan of a search region by a laser beam is finished, a laser beam angle is determined from the rate attenuation of laser light in the atmosphere, the minimum detectable target shape, and the longest detectable distance and a laser beam angle is made variable so that the laser beam angle for the next scan becomes equal to the determined laser beam angle.

According to a still further aspect of the present invention, there is provided a laser beam shaper for changing the shape of a laser beam inputted thereto, comprising a concave objective mirror and a convex objective mirror provided on the same optical axis, and means for changing a relative distance between the concave objective mirror and the convex objective mirror.

A relation between a detectable distance R and a laser beam angle $\theta_t$ is obtained from the following radar equation:

$$P_r = \frac{4 P_o K_t A_r A_t \delta T(R)^2}{\pi^2 (D + \theta_t R)^2 R^2} \cdot \cdot \quad (1)$$

The equation (1) holds for the case of $(\theta_t R)^2 \pi > A_t$. In the equation (1), $P_o$ is the laser output, $K_t$ the efficiency of a transmitting system, $K_r$ the efficiency of a receiving system, $A_r$ the aperture of the receiving system, $A_t$ the cross section area of a target, $D$ the aperture of the transmitting system, $\delta$ the reflection coefficient, and $P_r$ the received power. Usually, because of $D << \theta_t R$, the equation (1) can be approximated as follows:

$$P_r = \frac{4P_o K_t K_r A_r \delta}{\pi^2 \theta_t^2 R^4} \cdot T(R)^2. \quad (2)$$

Accordingly, the rate of attenuation of laser light in the atmosphere can be written by $T(R) = e^{-\alpha_t R}$ where $\alpha_t$ is the attenuation coefficient [1/km]. Thus, the rate of attenuation $T(R)$ is represented by the attenuation coefficient $\alpha_t$ which is different depending on the wavelength of laser light used as well as meteorological conditions and the detectable distance R.

Provided that the minimum sensitivity of a light detector is $P_s$, the target can be detected if the received power $P_o$ obtained from the equation (2) is larger than $P_s$. The quantities which can be controlled by the laser radar is the laser output $P_o$ and the laser beam angle $\theta_t$. In the case where the rate of attenuation $T(R)$ becomes large ($P_s > P_r$) so that the target cannot be detected, it is possible to make $P_o$ large or to make $\theta_t$ small, as is apparent from the equation (2).

Provided that a search region angle is $\theta_s$, it is not necessary to scan a laser beam in the case of $\theta_s \leq \theta_t$. However, in the case of $\theta_s > \theta_t$, the beam scan is required and hence it is preferable to make $\theta_t$ as large as possible.

Thus, if $\theta_t$ is determined from the equation (2), a laser radar having a fixed detectable distance is obtained.

Namely, by solving the equation (2) with respect to $\theta_t$, the following equation is obtained:

$$\theta_t = \frac{\sqrt{4P_o K_t K_r A_r}}{\sqrt{P_r} \pi} \cdot \frac{\sqrt{A_r \delta}}{R^2} T(R). \quad (3)$$

If the required longest detectable distance $R_{max}$ and the required minimum detectable shape $A_{min}$ are introduced into the equation (3) in place of the detectable distance R and $A_r \cdot \delta$, respectively, a laser beam angle $\theta_t$ is obtained at which a detectable distance is fixed as the longest detectable distance $R_{max}$ irrespective of any change of the rate of attenuation $T(R)$. However, the rate of attenuation $T(R)$ of laser light in the atmosphere is an unknown quantity.

Accordingly, a laser radar according to the present invention is provided with means for estimating the rate of attenuation $T(R)$ of laser light and determining a laser beam angle $\theta_t$ from the equation (3) on the basis of the laser output $P_o$, the longest detectable distance $R_{max}$, the minimum detectable cross section area $A_{min}$ of the target and the estimated rate of attenuation $T(R)$, and means for shaping a laser beam so as to provide the determined laser beam angle $\theta_t$, whereby the desired longest detectable distance $R_{max}$ can be obtained even if the rate of attenuation $T(R)$ of laser light in the atmosphere changes depending on the meteorological conditions.

The estimation of the attenuation coefficient of laser light is made by measuring a visibility range and determining the rate of attenuation from the measured visibility range. Alternatively, the rate of attenuation can be estimated by transmitting a laser beam toward a structure placed at a specified distance from the laser radar in the course of search for the target to determine the rate of attenuation from waves reflected from the structure. Further, the rate of attenuation coefficient can be estimated by measuring the atmospheric temperature, humidity, atmospheric pressure and rainfall and determining the rate of attenuation coefficient of laser light in the atmosphere from the measured atmospheric temperature, humidity, atmospheric pressure and rainfall.

When the determined laser beam angle is wider than a search region where a search for the target is to be made, the laser beam angle is made to coincide with the search region. Thereby, the intensity of the reflected waves from the target can be enhanced. On the other hand, when the determined laser beam angle is smaller than a converging limit of the laser beam, the laser beam angle is made coincident with the converging limit. Thereby, it is possible to prevent the laser beam angle from falling below the converging limit of the laser beam and hence the search for the target can be surely made.

Also, in a scanning method for a laser radar according to the present invention, each time the scan of a search region by a laser beam is finished, a laser beam angle is determined and a laser beam angle is made variable for the next scan. Since the laser beam angle is not changed in the course of the linear scanning, the whole of the search region can be surely raster-scanned.

Further, in a laser beam shaper according to the present invention, a structure is employed which allows for a change in a relative distance between a concave objective mirror and a convex objective mirror. Since the reflecting mirror has a high resistance against energy as compared with a lens, it can cope with high energy.

DESCRIPTION OF THE PREFERRED EMBODIMENTS

Embodiments of the present invention will now be explained referring to the accompanying drawings.

Figure 1:
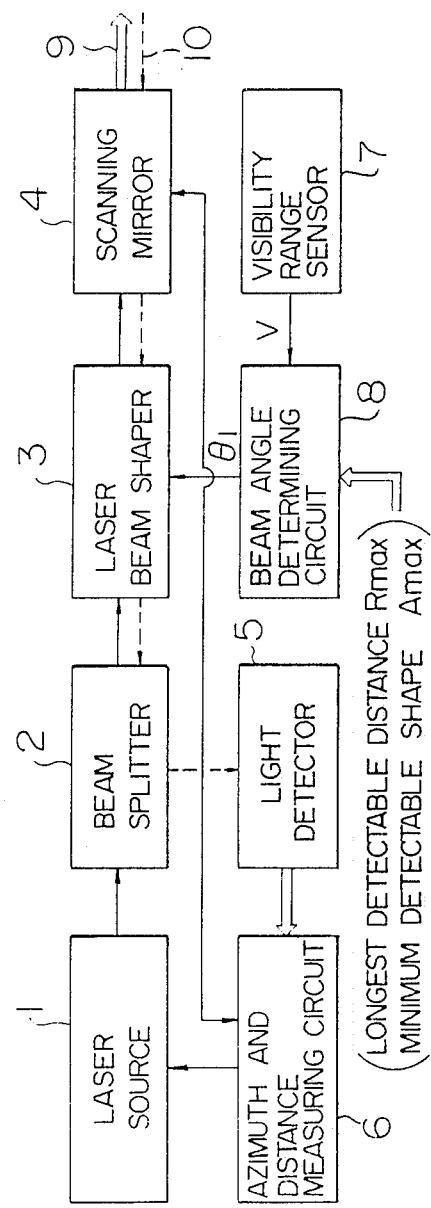
FIG. 1 is a schematic block diagram of a laser radar according to an embodiment of the present invention.

In FIG. 1 showing an embodiment of the present invention, a laser radar comprises a laser source 1 for a laser beam to be transmitted, a beam splitter 2, a laser beam shaper 3, a scanning mirror 4 for scanning the laser beam in a search region, a light detector 5 for detecting light reflected from a target, an azimuth and distance measuring circuit 6 for measuring the azimuth of the target and a distance to the target on the basis of an output of the light detector 5 and the scanning angle of the scanning mirror 4, a visibility range sensor 7 for measuring a visibility range, and a beam angle determining circuit 8 for determining a laser beam angle $\theta_t$ from an output V of the visibility range sensor 7, the longest detectable distance $R_{max}$ of the target and the minimum detectable shape $A_{min}$ of the target.

Laser light emitted from the laser source 1 enters the laser beam shaper 3 through the beam splitter 2. In the laser beam shaper 3, the laser beam is shaped so as to provide the laser beam angle $\theta_t$ determined by the beam angle determining circuit 8. A transmission laser beam 9 outputted from the laser beam shaper 3 is scanned in the search region by the scanning mirror 4. The transmission laser beam 9 impinges upon the target and light 10 reflected waves from the target is introduced into the light detector 5 by the beam splitter 2 through the scanning mirror 4 and the laser beam shaper 3. The azimuth of the target can be detected on an output of the light detector 5 and the scanning angle of the scanning mirror 4 and the distance to the target can be measured by measuring a propagation time from the transmission of the laser light to the reception of the reflected waves.

In the beam angle determining circuit 8, the laser beam angle $\theta_t$ is determined as follows.

As has already been mentioned, $\theta_t$ is determined from the following equation (3):

$$\theta_t = \frac{\sqrt{4P_o K_t K_r A_r}}{\sqrt{P_r} \; \pi} \cdot \frac{\sqrt{A_t \delta}}{R^2} \, T(R). \tag{3}$$

If the required longest detectable distance $R_{max}$ and the required minimum detectable shape $A_{min}$ are introduced into the equation (3) in place of the detectable distance R and $A_r \cdot \delta$, respectively, a laser beam angle $\theta_t$ is obtained at which a detectable distance is fixed as the longest detectable distance $R_{max}$ irrespective of any change of the rate of attenuation T(R) of laser light in the atmosphere. The rate of attenuation T(R) of laser light in the atmosphere is an unknown quantity and is given by the following equation:

$$T(R) = e^{-\alpha_t R} \tag{4}$$

where $\alpha_t$ is the attenuation coefficient. If $\alpha_t$ is known, the rate of attenuation T(R) can be determined by equation (4). However, it is not possible to directly measure $\alpha_t$. The rate of attenuation T(R) of laser light in the atmosphere and the visibility range V satisfy therebetween the following relation:

$$T(R) = \exp\{-3.91 R/V(0.55/\lambda)^p\} \tag{5}$$

where $\lambda$ is the wavelength of laser light and P is equal to 1.3 in the case of $V \geq 6$ km and $0.585^{\frac{1}{3}}$ in the case of $V < 6$ km. As is apparent from the equation (5), T(R) can be determined if V is measured by the visibility range sensor 7.

In this manner, according to the present embodiment, a laser radar can be constructed in which each of the longest detectable distance and the minimum detectable shape (cross section area) are fixed even if the rate of attenuation of laser light changes.

Next, an explanation will be made of another embodiment of the present invention. In the present embodiment, an additional function which will be mentioned hereinbelow is provided for the beam angle determining circuit 8 in the embodiment shown in FIG. 1.

Figure 2:
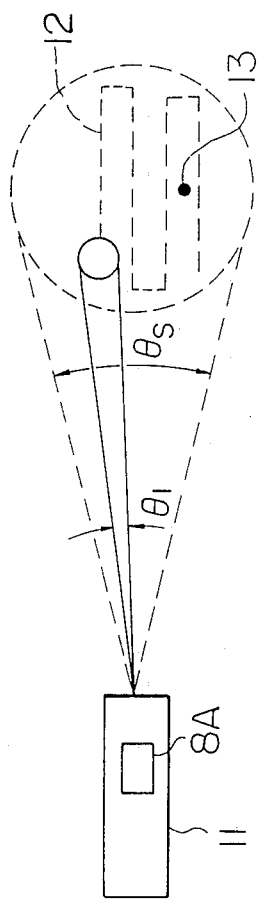
FIG. 2 is a view showing a relationship between a laser radar, a transmission laser beam angle and a search region angle for explaining another embodiment of the present invention.

As is shown in FIG. 2, in a laser radar 11 of the present embodiment, in the case where a laser beam angle $\theta_t$ is determined and a search for a target 13 is made in a range of a search region angle $\theta_s$, the span of $\theta_s$ is scanned along a scanning path 12 indicated in FIG. 2 in the case of $\theta_t < \theta_s$. In the case of $\theta_s \leq \theta_t$, it is not necessary to scan laser light. Accordingly, in a beam angle determining circuit 8A, $\theta_t$ determined by the equation (3) is compared with $\theta_s$ and $\theta_t$ is set to be equal to $\theta_s$ in the case of $\theta_s \leq \theta_t$. Thereby, $\theta_t$ is prevented from expanding with a span larger than $\theta_s$. As a result, the intensity of the reflected waves 10 from the target 13 in the case of $\theta_s \leq \theta_t$ can be made higher than that in the case of $\theta_t > \theta_s$.

The laser beam angle $\theta_t$ has the minimum converging limit which depends on the aperture D of the laser beam shaper 3 and the conditions of the atmosphere. For simplification of explanation, consider a Gaussian beam the intensity distribution which exhibits a Gaussian distribution in a radius direction. The converging limit $\theta_{limit}$ in that case is given by the following equation:

$$\theta_{limit} = \sqrt{\left(\frac{2\sqrt{2} \, \lambda}{\pi D}\right)^2 + (2.01 \lambda^{-1/5} C_n^{6/5} R^{3/5})^2} \tag{6}$$

where $\lambda$ is the wavelength of laser light, D the aperture diameter, and $C_n$ is the refractive index structure constant. It is not possible to make the laser beam angle $\theta_t$ smaller than $\theta_{limit}$. Therefore, in the beam angle determining circuit 8A, $\theta_t$ determined by the equation (3) is compared with $\theta_{limit}$ and $\theta_t$ is set to be equal to $\theta_{limit}$ in the case of $\theta_t < \theta_{limit}$.

Figure 3:
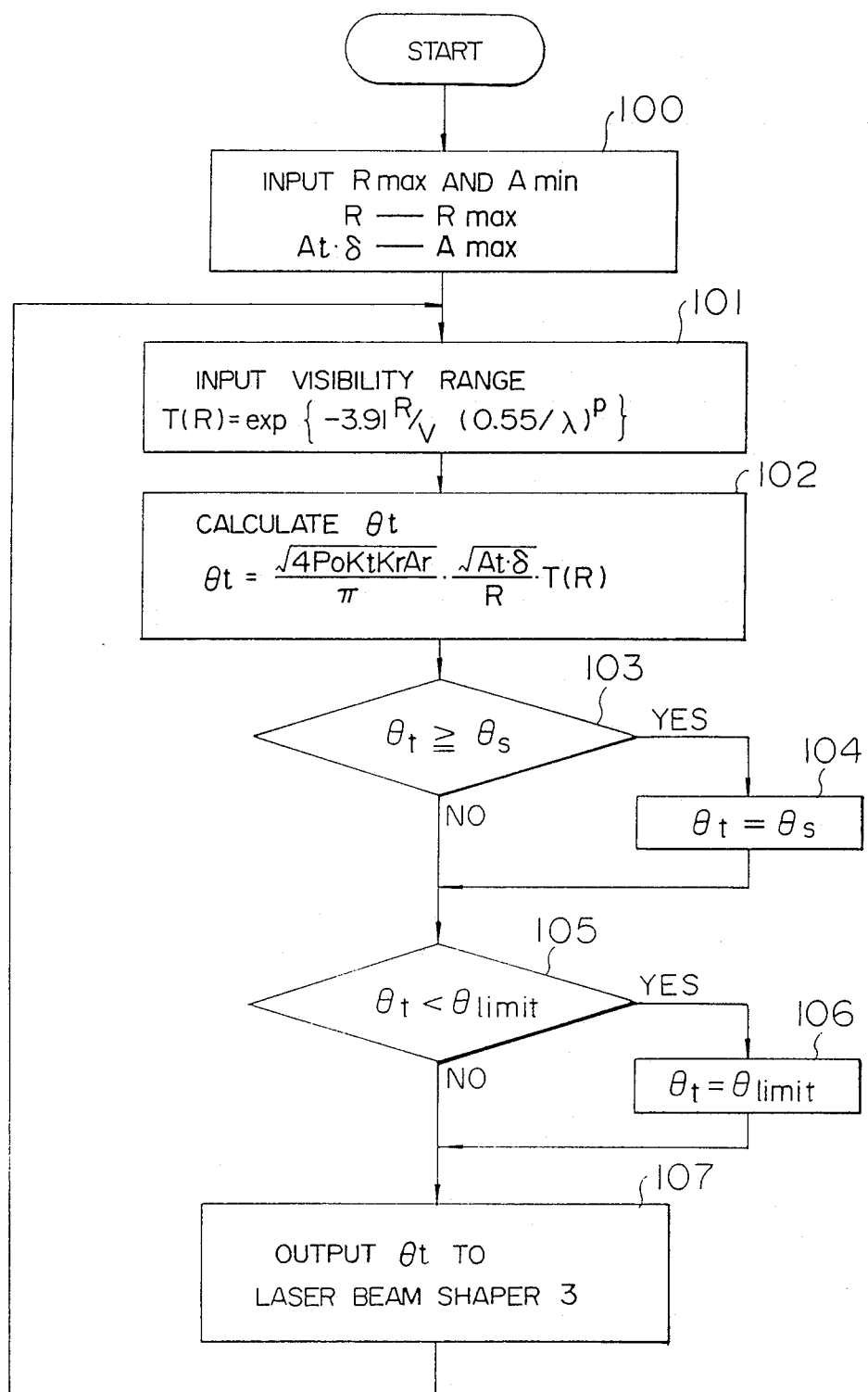
FIG. 3 is a flow chart for explaining the operation of the beam angle determining circuit which is used in a laser radar according to the embodiment explained in conjunction with FIG. 2.

A flow chart showing the contents of the above-explained control performed by the beam angle determining circuit 8A is illustrated in FIG. 3. In steps 100, 101 and 102, the laser beam angle $\theta_t$ is determined in a manner mentioned above. In step 103, the judgement is made of whether or not $\theta_t$ is smaller than $\theta_s$. In the case of $\theta_t \geq \theta_s$, $\theta_t$ is set to be equal to $\theta_s$ (step 104). In step 105, the judgement is made of whether or not $\theta_t$ is smaller than $\theta_{limit}$. In the case of $\theta_t < \theta_{limit}$, $t$ is set to be equal to $\theta_{limit}$ (step 106). In step 107, $\theta_t$ thus determined is outputted to the laser beam shaper 3.

With the above construction, not only can the intensity of reflected waves from the target be enhanced but also it is possible to prevent the laser beam angle from falling below the converging limit of the laser beam, thereby allowing a sure search for the target.

Next, still another embodiment of the present invention in which the laser beam angle $\theta_t$ is determined by estimating the rate of attenuation T(R) of laser light in the atmosphere, will be explained by virtue of FIG. 4. Components in FIG. 4 having the same reference numerals as the components shown in FIG. 1 represent equivalent components to those in FIG. 1.

Figure 4:
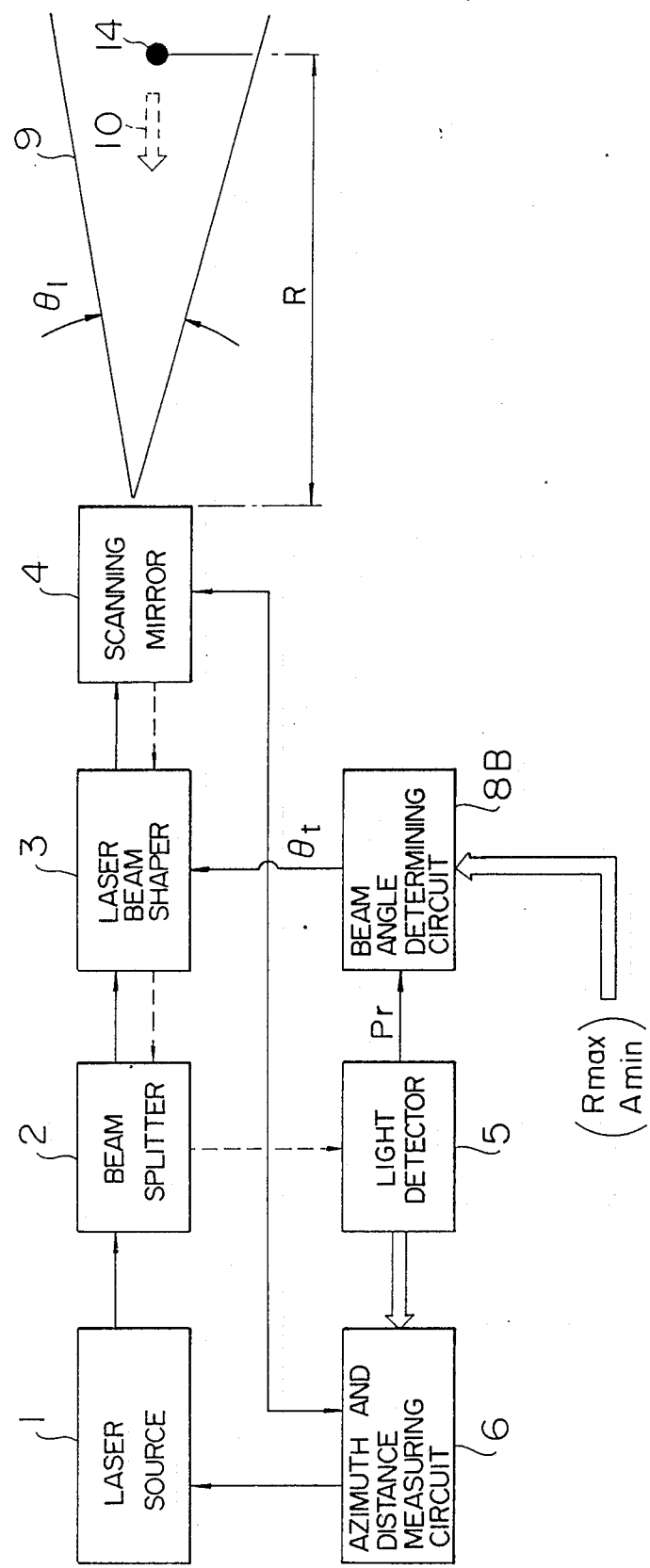
FIG. 4 is a schematic block diagram of a laser radar according to still another embodiment of the present invention.

In a laser radar according to the present embodiment, a dummy target 14 as shown in FIG. 4 having a known distance R thereto and a known shape $A\delta$ thereof is used to measure the rate of attenuation of laser light in the atmosphere during a predetermined period of time before a search is made or when a search is being made.

The operation of the present embodiment will now be described. First, a command value $\theta_t = \theta_1$ for the laser beam angle is inputted from a beam angle determining circuit 8B to a laser beam shaper 3 to transmit a laser beam 9 toward the dummy target 14. Reflected waves 10 from the dummy target 14 are received by a light detector 5 through a scanning mirror 4, the laser beam shaper 3 and a beam splitter 2. In the light detector 5, the received power $P_r$ of the reflected waves 10 is measured and $P_r$ is outputted to the beam angle determining circuit 8B. In the beam angle determining circuit 8B, the rate of attenuation T(R) is calculated by use of the equation (1) from the following equation:

$$T(R) = \frac{\pi \theta_1 R^2}{\sqrt{4 P_o K_t K_r A_r \delta}} \cdot \sqrt{P_r} \ . \quad (7)$$

Since T(R) is thus known, $\theta_t$ can be determined from the equation (3) as follows:

$$\theta_t = \frac{\sqrt{4 P_o K_t K_r A_r}}{\sqrt{P_r \ \pi}} \cdot \frac{\sqrt{A_{min}}}{R^2_{max}} \cdot T(R). \quad (8)$$

As is apparent from the foregoing, according to the present embodiment, $\theta_t$ can be determined by use of a function inherent to the laser radar.

Next, explanation will be made of a further embodiment of the present invention in which the rate of attenuation T(R) of laser light in the atmosphere is estimated from the atmospheric temperature, humidity, atmospheric pressure, and so on. The cause of the attenuation of laser light in the atmosphere includes the absorption and scattering of laser light by particles existing in the atmosphere. The particles in the atmosphere include aerial molecules, aerosols, water drops (fog drops and rain drops), and so on. The absorption by particles which is one factor of the attenuation of laser light is mainly caused in an infrared wavelength region by aqueous vapor $H_2O$ and carbonic acid gas $CO_2$. The concentration of $CO_2$ in the atmosphere is substantially constant irrespective of the weather. On the other hand, the absorption by $H_2O$ is governed by the amount of condensed water which is determined by the atmospheric humidity and temperature.

The scattering by particles which is the other factor of the attenuation of laser light includes Rayleigh scattering or Mie scattering, depending on a relationship between the size of particles and the wavelength of laser light. The Rayleigh scattering occurs in the case where the particle size is small as compared with the wavelength. The Mie scattering occurs when the particle size is large, and the dependency of the scattering amount on the wavelength is extinguished in the case where the particle size is larger than the wavelength.

As has been explained above, the attenuation of laser light in the atmosphere is caused by the absorption and scattering of laser light by particles in the atmosphere. Accordingly, if the amount of particles in the atmosphere can be measured, the rate of attenuation T(R) of laser light in the atmosphere can be calculated.

The amount of particles in the atmosphere changes depending on the wavelength, humidity, rainfall, atmospheric temperature and atmospheric pressure. The rate of attenuation T(R) in the atmosphere depending on those parameters is known and is described in many articles which include the following:

(1) E. A. Barndhardt & J. L. Street: "A Method for Prediting Atmospheric Aerosol Scattering Coefficients in the Infrared", Appl. Opt. 9, 1337 (1970);

(2) D. B. Rench & R. K. Long: "Comparative Studies of Extinction and Backscattering by Aerosols, Fog and Rain at 10.6 $\mu$ and 0.63$\mu$", Appl. Opt. 9, 7, 1563 (1970);

(3) T. S. Chu & D. C. Hogg: "Effects of Prediction at 0.63, 3.5 and 10.6 Microns", Bell Sys. Tech. J., 47, 723 (May-June, 1968); and (4) A. P. Medica & H. Kleiman: "Statistics of Global IR Atmospheric Transmission", MIT, ADA024311 (1976).

Figure 5:
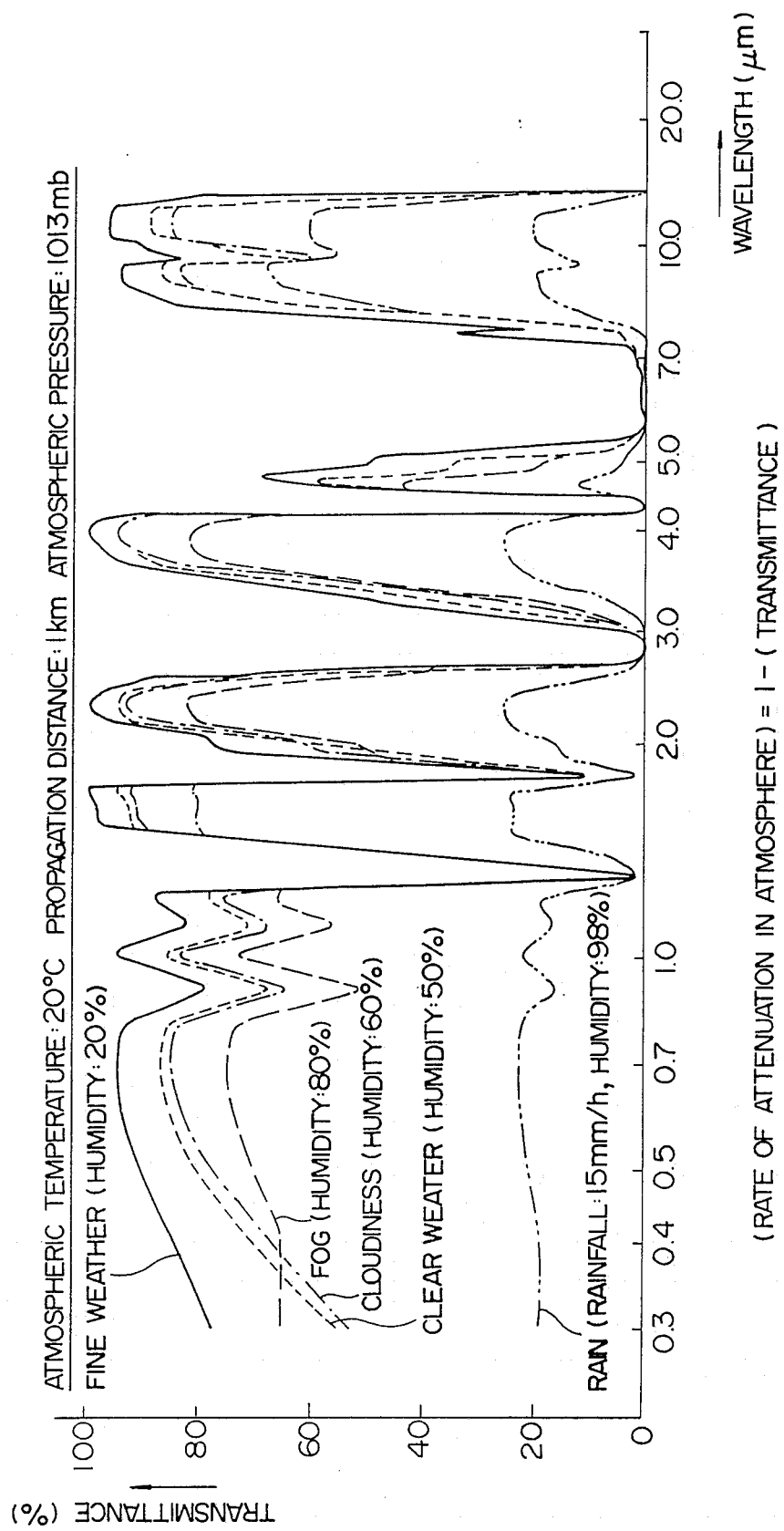
FIG. 5 is a graph showing a calculated relationship between the transmittance of laser light in the atmosphere and the wavelength of laser light with meteorological conditions taken as parameters for explaining a further embodiment of the present invention.

FIG. 5 shows the results of calculation of the transmittance [=1−(the rate of attenuation)] in the atmosphere at the atmospheric temperature of 20° C. and at the propagation distance of 1 km. As is apparent from FIG. 5, if the atmospheric temperature, humidity, rainfall and atmospheric pressure are known, the rate of attenuation T (R) in the atmosphere can be determined by calculation.

Figure 6:
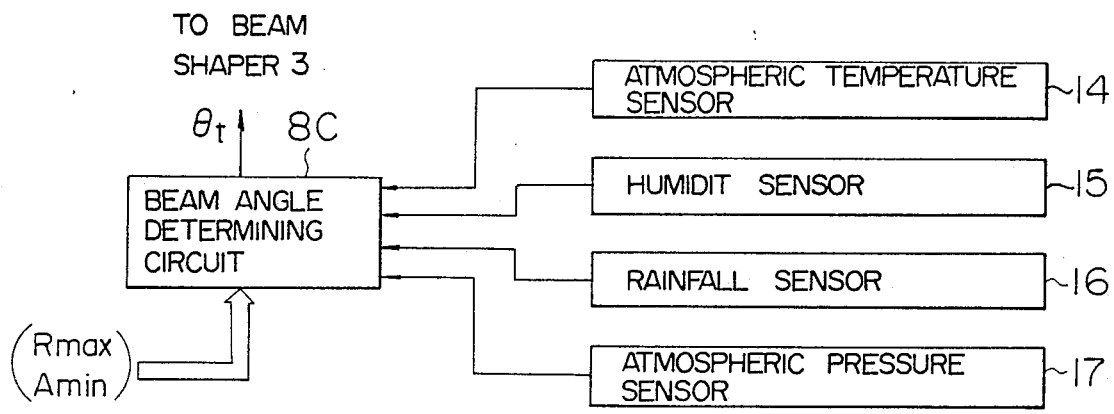
FIG. 6 is a schematic block diagram showing meteorological sensors and a beam angle determining circuit which are used in a laser radar according to the embodiment explained in conjunction with FIG. 5.

The embodiment of the present invention in which the rate of attenuation of laser light is determined on the basis of the above-mentioned principle, will now be explained by virtue of FIG. 6. As is shown, in the present embodiment, an atmospheric temperature sensor 14, a humidity sensor 15, a rainfall sensor 16 and an atmospheric pressure sensor 17 are provided. The results of measurement by those sensors are inputted to a beam angle determining circuit 8C to calculate the rate of attenuation from the transmittance as shown in FIG. 5 and the beam angle determining circuit 8C determines a laser beam angle $\theta_t$ and outputs it to the laser beam shaper 3 (see FIG. 1).

According to the present embodiment, each of the detectable distance and the detectable shape provided by a radar laser can be maintained to a constant value or a value larger than that even if the rate of attenuation T(R) in the atmosphere changes. Though in the shown embodiment one sensor is provided for each of the atmospheric pressure, atmospheric temperature, humidity and rainfall, it can be easily understood that a plurality of sensors may be provided at different locations for each of the atmospheric pressure, atmospheric temperature, humidity and rainfall in order to determine $\theta_t$ from the average value of the results of measurement at the different locations for each meteorological quantity.

Figure 7:
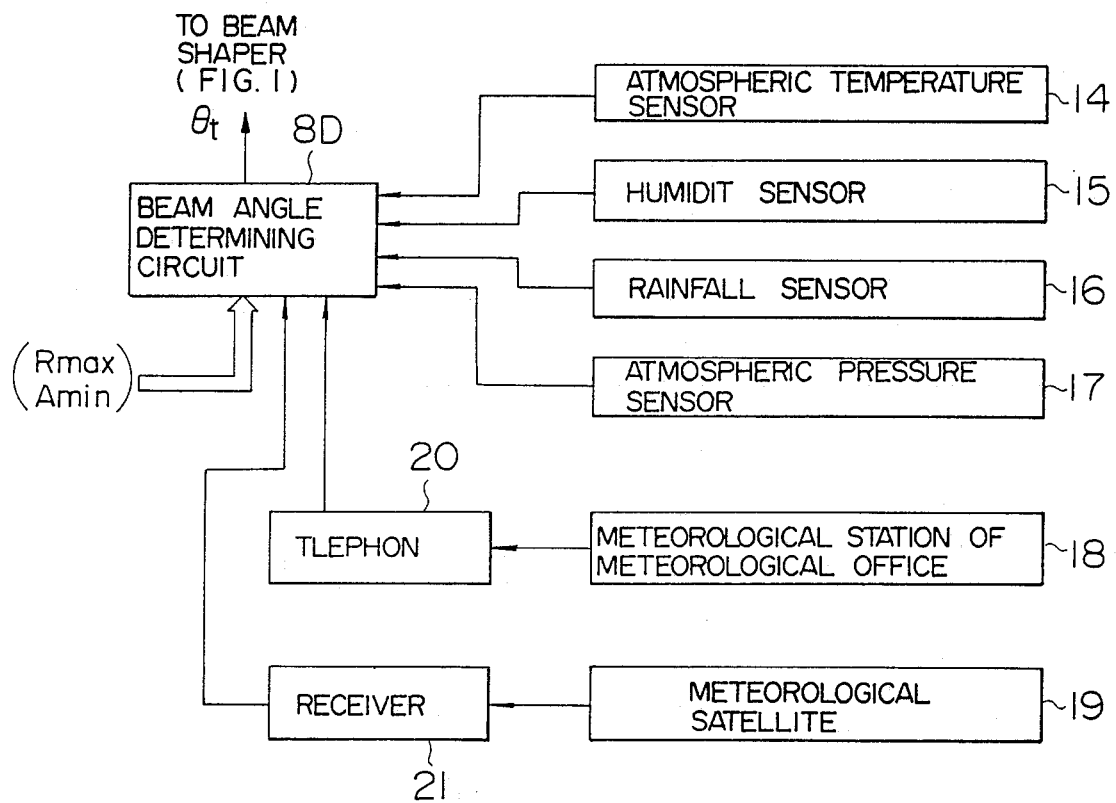
FIG. 7 is a schematic block diagram showing the main part of a laser radar according to a still further embodiment of the present invention.

Next, a still further embodiment of the present invention will be explained by virtue of FIG. 7. In the present embodiment, Meteorological data such as atmospheric temperature, humidity and so on are periodically measured at a meteorological station(s) 18 of the Meteorological Office and a meteorological satellite 19. Data from the meteorological station 18 of the Meteorological Office are received by a telephone 20 and inputted therefrom to a beam angle determining circuit 8D. Data from the meteorological satellite 19 which are being directly transmitted in a form of microwaves to the earth, are received by a receiver 21 and inputted therefrom to the beam angle determining circuit 8D. According to the present embodiment, since meteorological data of a very wide range including data from the meteorological station 18 and the meteorological satellite 19 in addition to local data from sensors inclusive of an atmospheric pressure sensor 14 and so on are obtained, the accuracy of estimation of the rate of attenuation T(R) in the atmosphere can be improved.

In principle, a laser radar can measure the atmospheric temperature, humidity and atmospheric pressure. Explanation will now be made of an additional embodiment of the present invention in which $\theta_t$ is made variable by measuring meteorological data in the course of a search for the target 13.

Figure 8:
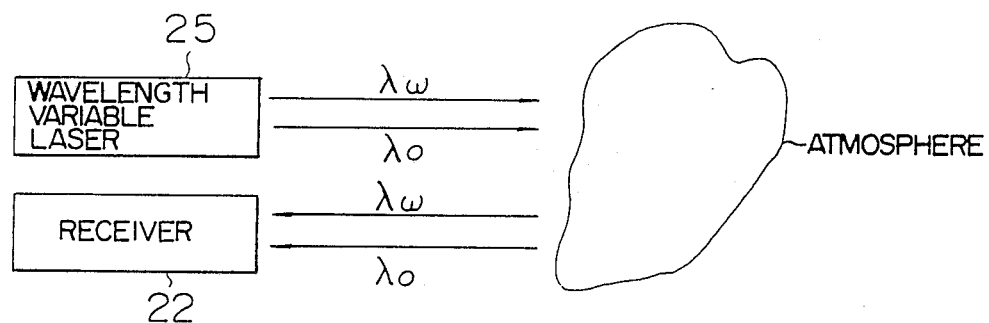
FIGS. 8 and 9 are views showing the principle of a differential absorption technique for explaining an additional embodiment of the present invention.
Figure 9:
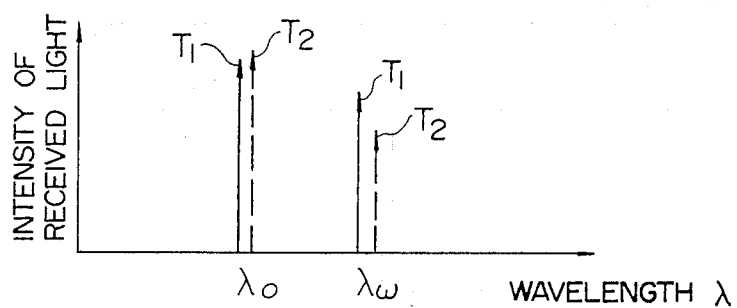

The measurement of meteorological data by a laser radar can be carried out by mans of a differential absorption technique. The principle of the differential absorption technique will now be explained by use of FIGS. 8 and 9. First, laser light having a wavelength of $\lambda_o$ is transmitted into the atmosphere from a wavelength variable laser 22 which can generate two kinds of laser lights having wavelengths of $\lambda_o$ and $\lambda_w$. A reflected version of the transmitted laser light is received by a receiver 22 to measure the intensity of the reflected light. Thereafter, the same process is repeated for laser light having a wavelength of $\lambda_w$. As the wavelength $\lambda_w$ is selected one at which the rate of change in laser light absorption coefficient for a change of each of the atmospheric temperature, humidity and atmospheric pressure is large. On the other hand, as the wavelength $\lambda_o$ is selected one which is near to $\lambda_w$ but at which the change rate absorption coefficient is different from the change rate at $\lambda_w$. The value of each of the temperature, humidity and pressure can be determined from the intensity of the reflected light of $\lambda_w$ while the intensity of the reflected light of $\lambda_o$ is used for making subtractive compensation for absorption or scattering by the background. FIG. 9 shows the intensities of reflected or received lights of $\lambda_o$ and $\lambda_w$ at the atmospheric temperatures of $T_1$ and $T_2$. By way of example, $\lambda_o=7700Å$ and $\lambda_w=7690Å$ are preferable for measurement of the atmospheric temperature, $\lambda_o=7593Å$ and $\lambda_w=7602Å$ are preferable for measurement of the atmospheric pressure, and $\lambda_o=7400Å$ and $\lambda_w=7243Å$ are preferable for measurement of the humidity.

Figure 10:
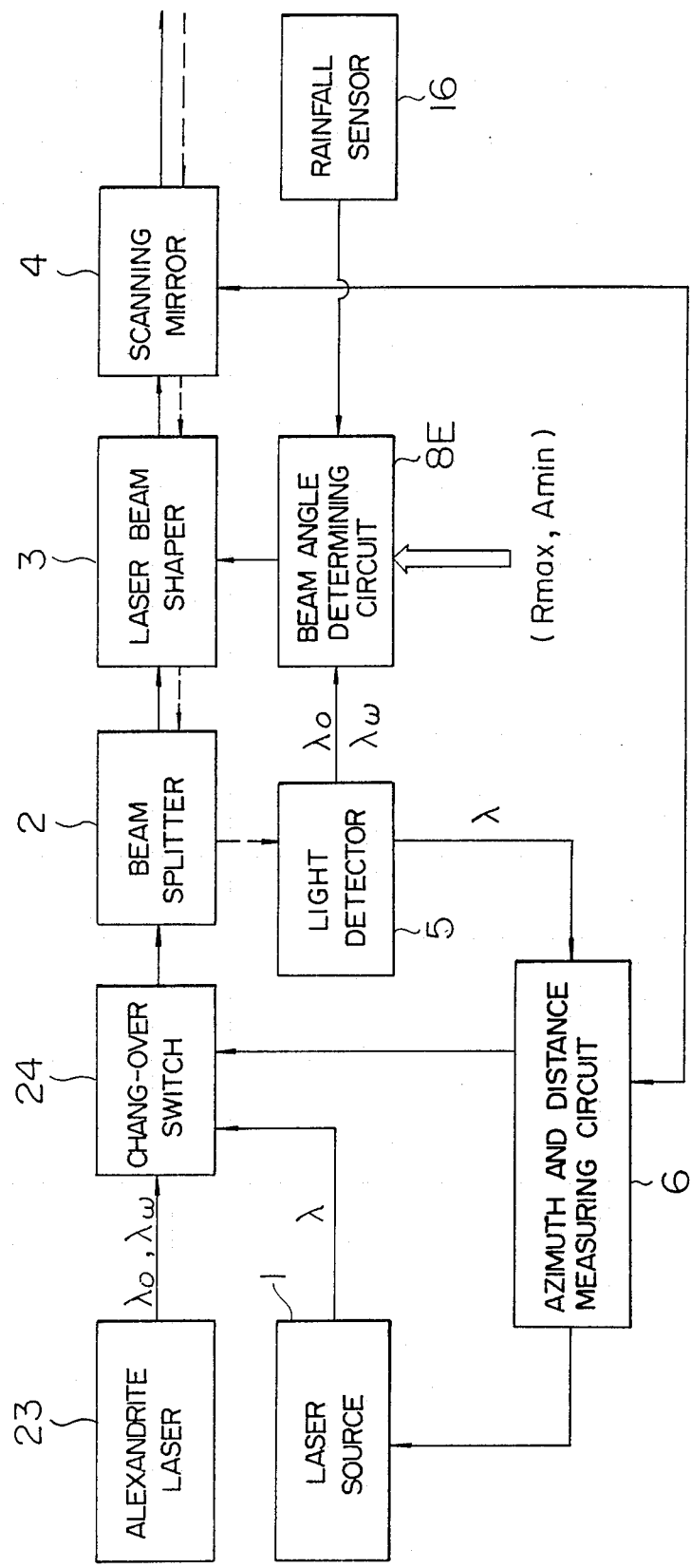
FIG. 10 is a schematic block diagram of a laser radar according to the embodiment explained in conjunction with FIGS. 8 and 9.

The embodiment of the present invention using the above-mentioned principle will now be explained by virtue of FIG. 10. Components in FIG. 10 having the same reference numerals as the components shown in FIG. 1 or 6 represent ones equivalent to the components in FIG. 1 or 6. Referring to FIG. 10, reference numeral 23 designates an alexandrite laser the oscillation wavelength of which can be changed in a range from 7100Å to 8100 Å, and numeral 24 designates a changeover switch for performing change-over between laser light from the alexandrite laser 23 and laser light from a laser source 1. In order to measure the atmospheric temperature, humidity and atmospheric pressure, laser lights with wavelengths of $\lambda_o$ and $\lambda_w$ for measurement of each meteorological quantity are generated from the alexandrite laser 23 and the intensities of reflected or received lights for the respective wavelengths $\lambda_o$ and $\lambda_w$ are measured by a light detector 5 and outputted therefrom to a beam angle determining circuit 8E. In the beam angle determining circuit 8E, the atmospheric temperature, humidity and atmospheric pressure are determined from the intensities of received lights corresponding to the respective meteorological quantities and the rainfall is inputted from a rainfall sensor 16. The beam angle determining circuit 8E determines the rate of attenuation T(R) in the atmosphere from those data to determine $\theta_t$. Thereafter, the switch 24 is changed over by a command from an azimuth and distance measuring circuit 6 so that the operation of a laser radar is performed by virtue of the laser light from the laser source 1.

According to the present embodiment, there can be constructed a laser radar in which the atmospheric temperature, humidity and atmospheric pressure can be measured without sensors for measurement of those quantities and the rate of attenuation is determined on the basis of those measurement values and data from the rainfall sensor so that $\theta_t$ is made variable in accordance with the rate of attenuation. The laser radar can always maintain an excellent detection performance.

Figure 11A:
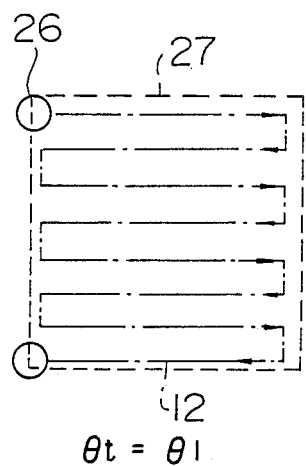
FIGS. 11A to 11C are views showing a scanning method for a laser radar according to an embodiment of the present invention.
Figure 11B:
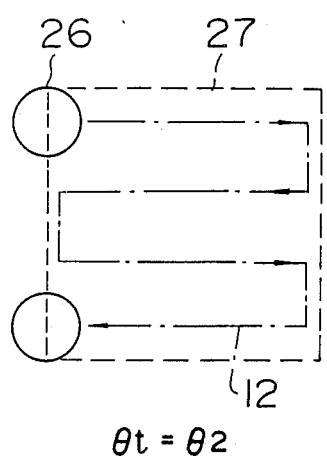
Figure 11C:
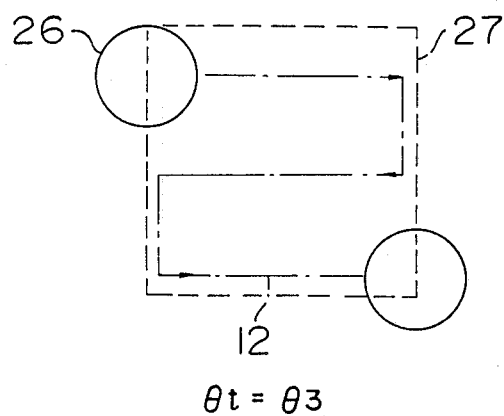

Next, a scanning method for a laser radar according to an embodiment of the present invention will be explained by virtue of FIGS. 11A to 11C. In the present embodiment, attention is paid to the timing at which a transmission laser beam angle $\theta_t$ is made variable. In the foregoing embodiments, means for determining $\theta_t$ from the rate of attenuation T(R) in the atmosphere has been explained. FIGS. 11A, 11B and 11C show a scanning path 12 in the respective cases where $\theta_t$ is $\theta_1$, $\theta_2$ and $\theta_3$ ($\theta_1<\theta_2<\theta_3$). In the case where during when the laser beam ($\theta_t=\theta_1$) scans a straight or linear path in a search region 27, a command of a different laser beam angle $\theta_t=\theta_2$ is issued from the beam angle determining circuit 8, 8B, 8C, 8D or 8E and the laser beam angle is changed, the scanning path 12 will assume a path which is not straight but folded, in order to make a search for the whole of the search region 27. Accordingly, even if the rate of attenuation T(R) in the atmosphere changes, $\theta_t$ should not be changed until the scan over the whole of the search region 27 is completed. The beam angle $\theta_t$ is changed at the point of time of completion of the scan. In this manner, a search for the whole of the search region 27 can be surely made through a raster scan shown in FIG. 11. Reference numeral 26 in FIG. 11 designates the cross section of the laser beam.

Figure 12:
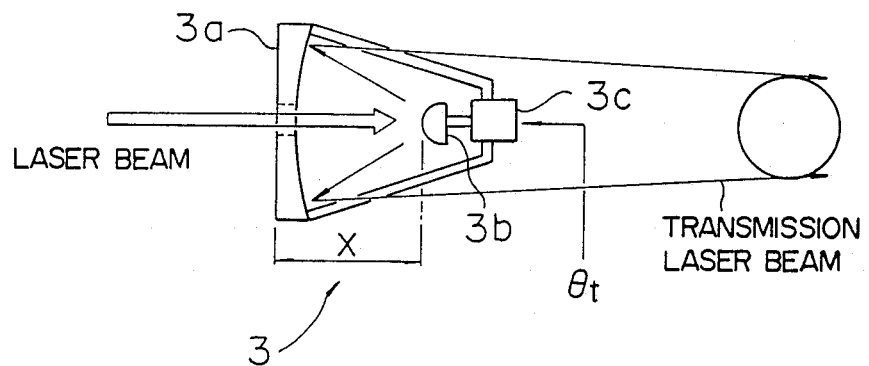
FIG. 12 is a schematic view showing the construction of a laser beam shaper according to an embodiment of the present invention.

Next, an embodiment of the laser beam shaper 3 will be explained by virtue of FIG. 12. In FIG. 12, the laser beam shaper 3 comprises a concave objective mirror 3a and a convex objective mirror 3b disposed on the same optical axis, and a beam angle controlling mechanism 3c. A laser beam passes through an aperture provided at a central portion of the concave objective mirror 3a and is reflected by the convex objective mirror 3b. The reflected beam is directed to the concave objective mirror 3a, is reflected again by the concave objective mirror 3a and is transmitted into the atmosphere. A distance x between the concave objective mirror 3a and the convex objective mirror 3b can be changed to make a laser beam angle $\theta_t$ variable. The beam angle controlling mechanism 3c is operatively connected to the convex objective mirror 3b so that the convex objective mirror 3b is moved relative the concave objective mirror 3a in a direction of the optical axis to provide the distance x conformable to a commanded angle $\theta_t$. In this manner, the distance x between the concave objective mirror 3a and the convex objective mirror 3b can be changed to control the beam angle $\theta_t$.

Though the above explanation has been made in conjunction with the case where the position of the convex objective mirror 3b, it is needless to say that the same effect can be obtained by changing the position of the concave objective mirror 3a. A zoom lens system of camera or the like is known as means for changing a laser beam angle. However, in the embodiment shown in FIG. 10, the reflecting mirrors are used. The reflecting mirror has a high resistance against energy. Therefore, the structure of this embodiment has an advantage that it can cope with a high energy laser.

According to the present invention, the rate of attenuation of laser light in the atmosphere which changes depending on meteorological conditions is measured and a laser beam angle providing a detection performance inclusive of a preset detectable distance and a preset detectable target shape is determined in accordance with the measured rate of attenuation. Therefore, the detection performance of the laser radar is not deteriorated depending on the meteorological conditions. If the laser beam angle is fixed, a detectable distance in the dry atmosphere in the winter season is twice or more as long as that in the wet atmosphere in the summer season. According to the present invention, the detectable distance can be kept constant.

Also, since the laser beam angle may be determined taking a target search region and a converging limit of the laser beam into consideration, not only the intensity of reflected waves from the target can be enhanced but also it is possible to prevent the laser beam angle from falling below the converging limit, thereby allowing a sure search for the target.

Further, since upon each completion of the scan of the search region by the laser beam the laser beam angle is made variable for the next scan, the whole of the search region can be surely raster-scanned.

Furthermore, since a laser beam shaper is constructed by a concave objective mirror and a convex objective mirror with a relative distance therbetween being variable, there can be provided a structure capable of coping with high energy.

We claim:

1. A method of detecting a target by scanning a laser beam in a predetermined region, comprising the steps of:
   determining a rate of attenuation of laser light propagating in the atmosphere;
   calculating a laser beam scan angle utilizing said determined rate of attenuation;
   controlling said laser beam in accordance with said calculated laser beam angle so as to scan said predetermined region; and
   detecting said target in said predetermined region in response to said scan of said predetermined region.

2. A method according to claim 1, wherein said rate of attenuation is detected by measuring a visibility range in the atmosphere.

3. A method according to claim 1, wherein said rate of attenuation is detected by use of a laser beam reflected from a structure placed at a specified distance from a reference.

4. A method according to claim 1, wherein said determining step determines said rate of attenuation utilizing at least one of the atmospheric temperature, humidity, atmospheric pressure and rainfall.

5. A method of detecting a target by scanning a laser beam in a predetermined region, comprising:
   detecting a distance to the target existing in said predetermined region in the atmosphere;
   calculating a laser beam scan angle utilizing said detected distance;
   controlling said laser beam in accordance with said calculated laser beam scan angle so as to scan said predetermined region; and
   detecting said target in said predetermined region in response to said scan or said predetermined region.

6. A method of detecting a target by scanning a laser beam in a predetermined region, comprising:
   detecting a shape of the target in said predetermined region in the atmosphere;
   calculating a laser beam scan angle utilizing said detected shape;
   controlling said laser beam in accordance with said calculated laser beam scan angle so as to scan said predetermined region; and
   detecting said target in said predetermined region in response to said scan of said predetermined region.

7. A laser radar for detecting a target by scanning a laser beam in a predetermined region, comprising:
   means for detecting the rate of attenuation of laser light propagating in the atmosphere;
   means for calculating a laser beam scan angle utilizing said detected rate of attenuation;
   means for controlling said laser beam in accordance with said calculated laser beam scan angle so as to scan said predetermined region; and
   means for detecting said target in said predetermined region in response to said scan of said predetermined region.

8. A laser radar according to claim 7, wherein said rate of attenuation is detected by measuring a visibility range in the atmosphere.

9. A laser radar according to claim 7, wherein said rate of attenuation is detected by use of a laser beam reflected from a structure placed at a specified distance from a reference.

10. A laser radar according to claim 7, wherein said rate of attenuation is detected by use utilizing at least one of the atmospheric temperature, humidity, atmospheric pressure and rainfall.

11. A laser radar for detecting a target by scanning a lsaer beam in a predetermined region, comprising:
    means for detecting a distance to the target existing in said predetermined region in the atmosphere;
    means for calculating a laser beam scan angle utilizing said detected distance;
    means for controlling said laser beam in accordance with said calculated laser beam scan angle so as to scan said predetermined region; and
    means for detecting said target in said predetermined region in response to said scan of said predetermined region.

12. A laser radar for detecting a target by scanning a laser beam in a predetermined region, comprising:
    means for detecting the shape of the target existing in said predetermined region in the atmosphere;
    means for calculating a laser beam scan angle utilizing said detected shape;
    means for controlling said laser beam in accordance with said calaculated laser beam scan angle so as to scan said predetermined region; and
    means for detecting said target in said predetermined region in response to said scan of said predetermined region.

13. A laser radar for detecting a target by scanning a laser beam in a predetermined region, comprising:
   means for measuring a visibility range;
   means for detecting a rate of attenuation of laser light in the atmosphere from the measured visibility range and determining a laser beam angle on the basis of the determined rate of attenuation, a minimum detectable target shape and a longest detectable distance; and
   means for controlling a laser beam angle so that it becomes equal to the determined laser beam angle.

14. A laser radar according to claim 13, wherein the laser beam angle determining means further includes means for determining a search region where a search for the target is to be made; means for calculating a converging limit of the laser beam; and means for controlling the laser beam angle so as to be coincident with said search region when the determined laser beam angle is wider than said search region, and making the laser beam angle coincident with said converging limit when the determined laser beam angle is smaller than said converging limit.

15. A laser radar for detecting a target by scanning a laser beam in a predetermined region, comprising:
   means for transmitting a laser beam toward a structure placed at a specified distance from the laser radar; means for determining the rate of attenuation of laser light in the atmosphere from waves reflected from the structure; means for determining a laser beam angle on the basis of the determined rate of attenuation, a minimum detectable target shape and a longest detectable distance; and
   means for controlling a laser beam angle so that it becomes equal to the determined laser beam angle.

16. A laser radar for detecting a target by scanning a laser beam in a predetermined region, comprising:
   means for measuring the atmospheric temperature, humidity, atmospheric pressure and rainfall;
   means for determining a rate of attenuation of laser light in the atmosphere from the measured atmospheric temperature, humidity, atmospheric pressure and rainfall; means for determining a laser beam angle utilizing the determined rate of attenuation, a minimum detectable target shape and a longest detectable distance; and
   means for controlling a laser beam angle so that it becomes equal to the determined laser beam angle.

17. A scanning method for detecting a target by scanning a laser beam in a predetermined region comprising the steps of:
   conducting a scan of a search region by a laser beam;
   calculating a laser beam angle from a rate of attenuation of laser light in the atmosphere, a minimum detectable target shape, and a longest detectable distance; and controlling said laser beam so that the laser beam angle for subsequent scan is equal to the determined laser beam angle.

* * * * *